(12) United States Patent
Whang

(10) Patent No.: US 10,251,398 B2
(45) Date of Patent: Apr. 9, 2019

(54) IMPROVING SHELF LIFE AND COLOR PROFILE OF RESIN COMPOSITIONS WITH SILVER NANOPARTICLES

(71) Applicant: The Board of Regents of the University of Texas System, Austin, TX (US)

(72) Inventor: Kyumin Whang, Helotes, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 120 days.

(21) Appl. No.: 15/026,970

(22) PCT Filed: Oct. 2, 2014

(86) PCT No.: PCT/US2014/058927
§ 371 (c)(1),
(2) Date: Apr. 2, 2016

(87) PCT Pub. No.: WO2015/051194
PCT Pub. Date: Apr. 9, 2015

(65) Prior Publication Data
US 2016/0255839 A1 Sep. 8, 2016

Related U.S. Application Data

(60) Provisional application No. 61/885,637, filed on Oct. 2, 2013.

(51) Int. Cl.
*A01N 59/16* (2006.01)
*A61L 27/54* (2006.01)
(Continued)

(52) U.S. Cl.
CPC .............. *A01N 59/16* (2013.01); *A61K 6/007* (2013.01); *A61K 6/083* (2013.01); *A61L 15/24* (2013.01);
(Continued)

(58) Field of Classification Search
None
See application file for complete search history.

(56) References Cited

U.S. PATENT DOCUMENTS 2,833,753 A * 5/1958 Joginder ................... C08F 4/00
502/167
3,672,942 A * 6/1972 Neumann et al. ... B22D 31/005
427/295
(Continued)

OTHER PUBLICATIONS

Fan et al., "Development of an antimicrobial resin—A pilot study", Dental Materials, vol. 27, Issue 4, pp. 322-328, 2011.

*Primary Examiner* — Peter A Salamon
(74) *Attorney, Agent, or Firm* — Winstead PC

(57) ABSTRACT

Methods of forming antimicrobial resin compositions comprising silver nanoparticles are disclosed, wherein the resin compositions that are generated exhibit lower initial color, reduced color shift upon storage and reduced levels of spontaneous polymerization. Such methods generally comprise: combining a silver-containing material with a self-cure and dual-cure base resin in situ wherein the base resin does not contain a catalytic amine; and adding a catalytic resin to the mixture of the resin and silver-containing material in order to form the final cured resin. Antimicrobial polymeric materials formed by said methods are also disclosed.

4 Claims, 12 Drawing Sheets

DMAEMA + AgBz (A) INITIAL SOLUTION (B) SOLUTION OVER TIME

(51) Int. Cl.
*A61L 27/44* (2006.01)
*A61L 15/24* (2006.01)
*A61L 15/44* (2006.01)
*A61K 6/00* (2006.01)
*A61K 6/083* (2006.01)
*C09D 5/14* (2006.01)

(52) U.S. Cl.
CPC ............ *A61L 15/44* (2013.01); *A61L 27/446* (2013.01); *A61L 27/54* (2013.01); *C09D 5/14* (2013.01); *A61L 2300/104* (2013.01); *A61L 2300/404* (2013.01); *A61L 2400/12* (2013.01)

(56) References Cited

U.S. PATENT DOCUMENTS

| | | | | |
|---|---|---|---|---|
| 5,760,100 | A * | 6/1998 | Nicolson | G02C 7/049 351/159.33 |
| 6,267,590 | B1 * | 7/2001 | Barry | A61C 7/14 433/20 |
| 6,716,895 | B1 * | 4/2004 | Terry | A61L 27/34 523/122 |
| 6,759,431 | B2 * | 7/2004 | Hunter | A61K 9/0024 424/403 |
| 8,906,984 | B2 * | 12/2014 | Ajayan | C08J 3/20 523/223 |
| 2005/0013842 | A1 * | 1/2005 | Qiu | A61L 12/088 424/423 |
| 2005/0203237 | A1 * | 9/2005 | Cornelius Maria Dekkers | A01N 59/16 524/450 |
| 2007/0231295 | A1 * | 10/2007 | Hoppe | A61K 8/25 424/78.09 |
| 2008/0181931 | A1 * | 7/2008 | Qiu | A61L 12/088 424/429 |
| 2009/0074705 | A1 * | 3/2009 | Graham | A01N 59/16 424/78.17 |
| 2009/0324666 | A1 * | 12/2009 | Krongauz | A61L 27/34 424/409 |
| 2010/0120942 | A1 * | 5/2010 | Ajayan | C08J 3/20 523/122 |
| 2011/0306699 | A1 * | 12/2011 | Whang | A01N 59/16 523/113 |
| 2012/0328553 | A1 | 12/2012 | Jin | |
| 2016/0166738 | A1 * | 6/2016 | Tramontano | A61L 27/34 424/405 |

* cited by examiner

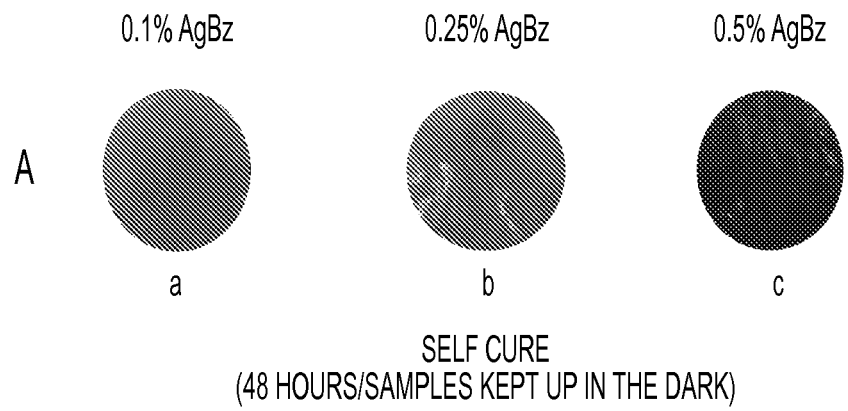
FIG. 10

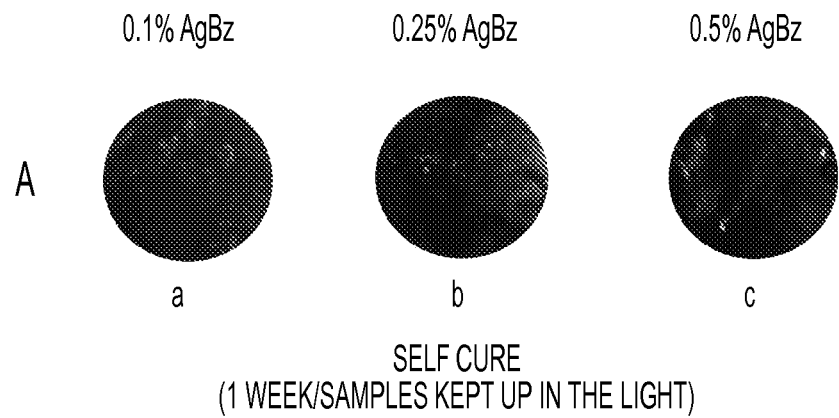
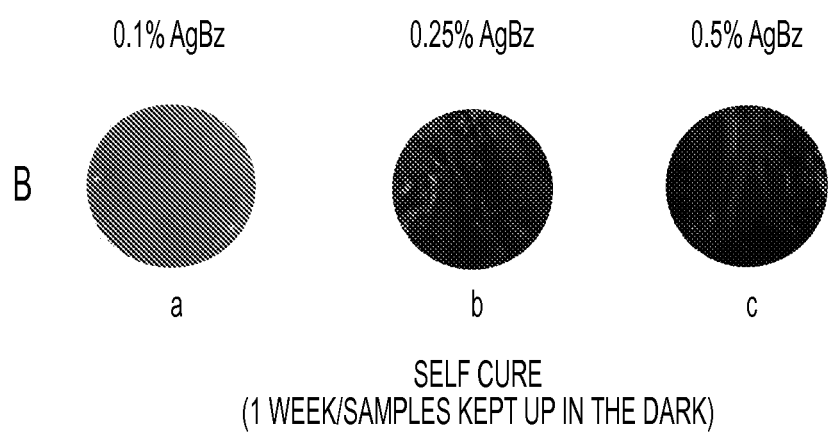
FIG. 11

IMPROVING SHELF LIFE AND COLOR PROFILE OF RESIN COMPOSITIONS WITH SILVER NANOPARTICLES

CROSS-REFERENCES TO RELATED APPLICATIONS

This application claims the benefit under 35 U.S.C. § 119(e) of U.S. Provisional Patent Application No. 61/885,637 filed Oct. 2, 2013, which is incorporated herein by reference in its entirety as if fully set forth herein. This application incorporates by reference, the entirety of U.S. patent application Ser. No. 13/162,454 filed Jun. 16, 2011.

TECHNICAL FIELD

This invention relates to a resin composition comprising silver particles that exhibits antimicrobial properties and improved shelf life color stability.

BACKGROUND OF THE INVENTION

Resin based restorative materials are the material of choice by doctors and patients due to their good mechanical properties, biocompatibility and aesthetic properties. A resin-based composition that possesses antimicrobial properties and inhibits microbial growth would be desirable. The applications that such an antimicrobial resin could be useful in include, products that can be used in medical applications including orthopedic applications and dental applications such as dental cements, luting agents and restorative materials. Various antibacterial agents have been incorporated into dental products such as rinse solutions, toothpastes, coatings, and dental resins to kill bacteria or inhibit bacterial growth, as well as in medical and other commercial products. Silver has been shown to be an effective antibacterial agent. However silver-based compositions often tend to be colored ("yellow" to "amber") and then "darken" or "blacken" upon storage and degrade the aesthetic appearance of these compositions rendering the material inapplicable to many products. Therefore, it would be desirable to create a silver-based resin composition that displays the antimicrobial properties of silver without the associated coloring and/or darkening or blackening.

SUMMARY OF THE INVENTION

An embodiment of the invention is directed to an antimicrobial resin composition containing silver particles and having a lower initial color (less yellow, more white) and reduced color shift, i.e., change in color over time.

A further embodiment of the invention is directed to methods for making an antimicrobial resin composition containing silver particles and having a lower initial color and reduced color shift over time.

Another embodiment of the invention is directed to a method for making an antimicrobial resin composition wherein a silver compound is mixed into the base resin (which contains the self-cure initiator) and stored in the dark or under "yellow light" prior to and during mixing with the catalyst resin.

Other embodiments of the invention are directed to methods of storing the cured resin in the dark or under "yellow light" to reduce color shift.

The foregoing has outlined rather broadly the features of the present disclosure in order that the detailed description that follows may be better understood. Additional features and advantages of the disclosure will be described hereinafter, which form the subject of the claims.

BRIEF DESCRIPTION OF THE DRAWINGS

FIGS. 5-6 demonstrate the color shift of the resin after the mixture of silver benzoate containing DMAEMA and the catalyst resin is mixed with the base resin and polymerized;

FIG. 10 demonstrates the effects of light on resin samples in the dark (A) and in the light (B);

FIG. 11 demonstrates the effects of light on resin samples in the light (A) and in the dark (B)

DETAILED DESCRIPTION OF EXEMPLARY EMBODIMENTS

Figure 1:
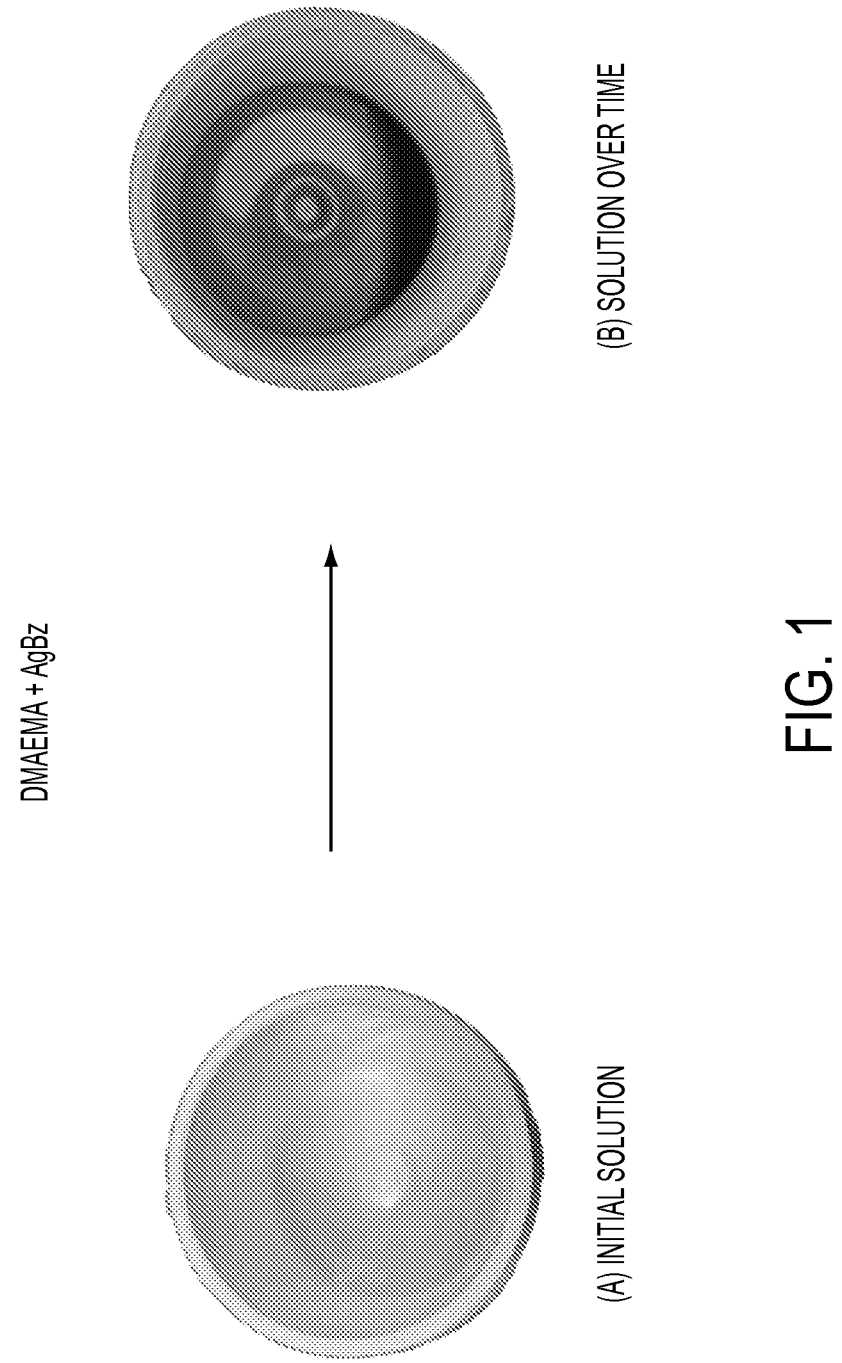
FIG. 1 shows the change in color of a silver benzoate solution over time.

In the following description, certain details are set forth so as to provide a thorough understanding of the present embodiments disclosed herein. However, it will be understood by those skilled in the art that the present disclosure may be practiced without such specific details. In many cases, details concerning such considerations and the like have been omitted inasmuch as such details are not necessary to obtain a complete understanding of the present disclosure and are within the skills of persons of ordinary skill in the relevant art.

The definitions and explanations as set forth herein are meant and intended to be controlling in any future construction unless clearly and unambiguously modified in the following Description or when application of the meaning renders any construction meaningless or essentially meaningless. In cases where the construction of the term would render it meaningless or essentially meaningless, the definition should be taken from Webster's Dictionary, 3rd Edition. Definitions and/or interpretations should not be incorporated from other patent applications, patents, or publications, related or not, unless specifically stated in this specification or if the incorporation is necessary for maintaining validity.

Other than in the operating examples, or where otherwise indicated, all numbers expressing quantities of components used herein are to be understood as modified in all instances by the term "about".

The present disclosure pertains to methods of forming antimicrobial resin compositions that comprise in situ generated silver nanoparticles. In some embodiments, the resin compositions are formed by combining a silver-containing material with a resin in situ and then curing the resin in the presence of the silver-containing material. Other aspects of the present disclosure pertain to antimicrobial resin compositions that comprise the above-mentioned in situ generated silver nanoparticles.

As used herein, the term, "antimicrobial" means that the article exhibits one or more of the following properties: the inhibition of the adhesion of bacteria or other microbes to the article; the inhibition of the growth of bacteria or other microbes on the article; and/or the killing of bacteria or other microbes on the surface of the article or in an area surrounding the article. For purposes of this invention, adhesion of bacteria or other microbes to the article, the growth of bacteria or other microbes on the article and the presence of bacterial or other microbes on the surface of the article are collectively referred to as "microbial colonization." In various embodiments, the articles of the present disclosure exhibit varying levels of inhibition of viable bacteria or other microbes. Such bacteria or other microbes include but are not limited to *Pseudomonas aeruginosa, Acanthamoeba* species, *Staphyloccus aureus, Escherichia coli, Staphyloccus epidermidis, Serratia marcesens, Acinetobacter baumannii* and/or the like.

As used herein, the term "patient" means and refers to a human or animal. Suitable examples include, but are not limited to a human or an animal (e.g., a dog, a cat, a horse, a bird, a reptile, an amphibian, a fish, a turtle, a guinea pig, a hamster, a rodent, a cow, a pig, a goat, a primate, a monkey, a chicken, a turkey, a buffalo, an ostrich, a sheep, a llama).

As used herein, the term "chemically feasible" refers to a connectivity of atoms such that the chemical valency of each atom is satisfied. For example, an oxygen atom with two bonds and a carbon atom with four bonds are chemically feasible.

As used herein, the term "nanoparticle(s)" means and refers to small particles ranging from small visible particles to particles on the nano-scale. As used herein, the term "metallic nanoparticle(s)" means and refers to nanoparticles that contain one or more metals, such as silver.

As used herein, the term "polymeric" means and refers to a composition(s) that comprises one or more monomers, oligomers, polymers, copolymers, or blends thereof. Suitable examples of polymers include, but are not limited to, polyvinyl alcohol, poly ethylene glycol, ethyl cellulose, polyolefins, polyesters, nonpeptide polyamines, polyamides, polycarbonates, polyalkenes, polyvinyl ethers, polyglycolides, cellulose ethers, polyvinyl halides, polyhydroxyalkanoates, polyanhydrides, polystyrenes, polyacrylates, polymethacrylates, polyurethanes, polypropylene, polybutylene terephthalate, polyethylene terephthalate, nylon 6, nylon 6,6, nylon 4,6, nylon 12, phenolic resins, urea resins, epoxy resins, silicone polymers, polycarbonates, polyethylene vinylacetate, polyethylene ethyl acrylate, polylactic acid, polysaccharides, polytetrafluoroethylene, polyvinylidenes, polyphosphazines, chlorinated polyethylenes, polysulfones and copolymers and blends thereof. It is also noted that the terms "polymeric", "polymer" and "resin" may be used interchangeably in the present disclosure.

As used herein, the term "water soluble" or use of the term "miscible in water" means and refers to a level of solubility such that when a composition is placed in water, greater than about 2.0 percent by weight of the composition dissolves. For example, methyl methacrylate (MMA) is considered substantially non water soluble, yet has a water solubility of about 1.6 g in 100 g of water.

Currently, polymeric materials, such as polymethyl methacrylate (PMMA), are used in many industries for numerous purposes. For instance, polymeric resin materials are used in dentistry, orthopedics and craniofacial surgery. However one major problem with the utilization of polymeric resin materials is the occurrence of infections (e.g., caries in dentistry). For example, but not by way of limitation, approximately 10% of soldiers returning from various battlefields develop infections after receiving craniofacial implants. Likewise, failure of orthopedic implants is often due to the periprosthetic infections of the PMMA bone cement. Current therapies to treat the more severe cases of infections involve the use of local and systemic antibiotics. However, antibiotic therapy poses the problem of generating resistant strains of bacteria. In the military, this is of special concern because many troops returning from various battlefields are infected with *Acinetobacter baumannii*, a multi-antibiotic resistant bacteria. Resin compositions of the claimed invention are also applicable in dental applications such as dental cements, luting agents and restorative materials. Furthermore, resin compositions of the claimed invention can be used in non-medical commercial applications as well.

Accordingly, antimicrobial agents have been added to many polymeric materials in order to prevent infections during their various uses. For instance, silver salts have been used in human healthcare and medicine as an antiseptic for post surgical infections. Silver salts have also been used as an anti-microbial agent for various purposes in dental devices, wound therapy, medical devices, and/or the like. Specifically, silver nitrate has been used to prevent ophthalmic neonatorum in newborns.

However, as discussed previously silver particle-containing polymers tend to be colored and/or tend to darken or blacken during storage and thus, tend to lose their aesthetic appeal. Accordingly, novel methods of forming antimicrobial polymeric materials and novel resulting products and compositions of matter that have improved shelf life and color profile relative to existing silver containing resin compositions have been developed. In some embodiments, the present disclosure provides methods of forming an antimicrobial resin composition that comprises a silver nanoparticle. Such methods generally comprise: combining a silver-containing material with a resin in situ wherein the resin does not contain a catalytic amine; and adding a catalytic resin to the mixture of the resin and silver-containing material in order to form the final cured resin.

By generating the metallic nanoparticle in situ, the monomer compositions can be cured more effectively with better nanoparticle dispersion than the prior art.

As explained below, numerous metal containing materials and resins may be used in various embodiments of the present disclosure. Likewise, various curing methods may be used to form the polymeric materials of the present disclosure.

Silver Containing Materials

A person of ordinary skill in the art will recognize that various silver containing materials may be used with the methods and compositions of the present disclosure. Specific examples include silver-containing materials (e.g., silver, silver alloys, silver oxides, silver carbides, silver nitrides, silver borides, silver borate, silver sulfides, silver myristates, silver stearates, silver oleates, silver gluconates, silver adipates, silver silicates, silver phosphides, silver halides, silver hydrides, silver nitrates, silver carbonates, silver sulfadiazines, silver acetates, silver lactates, silver citrates, alkali silver thiosulphates (e.g., sodium silver thio sulphate, potassium silver thio sulphate)).

In some embodiments, the silver containing materials are soluble in organic solvents and acrylic monomers. In more specific embodiments, metal containing materials may be silver oleates, silver gluconates, silver adipates, silver sulfadiazines, silver acetates, silver benzoate and the like. In further embodiments, the metal containing material is silver benzoate.

Resins

A person of ordinary skill in the art will also recognize that various resins may be used with the methods and compositions of the present disclosure. Non-limiting examples include acrylic resins. Acrylic resins include, but are not limited to, any resin containing an acrylate group (=CR—COOR'), where R and R' can be hydrogen, methyl, ethyl, butyl, benzoyl, or any alkyl or aryl group that is chemically feasible.

Other examples of resins that may be used with various embodiments of the present disclosure includes poly (methyl methacrylate) (PMMA) resins (an oil-based acrylic resin), other oil-based resins, water soluble resins, and/or the like.

More specific examples of resins that can be used with various embodiments of the present disclosure include, without limitation: Bis-GMA (bisphenol glycidyl methacrylate) based resins; TEGDMA (triethylene glycol dimethacrylate) based resins; HEMA (2-hydroxyethyl methacrylate) based resins; PMDM (pryomellitic acid diethylmethacrylate) based resins; PMGDM (pyromellitic acid glycerol dimethacrylate) based resins; UDMA (urethane dimethacrylate) based resins; methacrylate based resins; dimethacrylate based resins; hydrophobic resins; hydrophilic resins; and hardenable monomers suitable for dental and orthopedic applications.

Generally, oil-based resins are not soluble in water or have limited solubility in water such that less than about 2.0% by weight of the resin dissolves when placed in water. There are many types of oil-based resins that are suitable for the present disclosure. Specific examples of acrylic resins include, but are not limited to:

Poly(acrylonitrile-co-vinylidene chloride-co-methyl methacrylate):

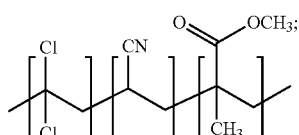

Poly(benzyl methacrylate):

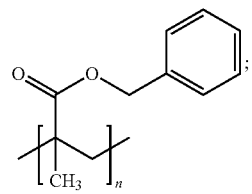

Poly(butyl methacrylate):

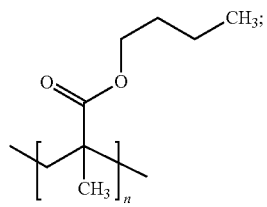

Poly(tert-butyl methacrylate):

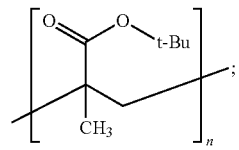

Poly(butyl methacrylate-co-isobutyl methacrylate):

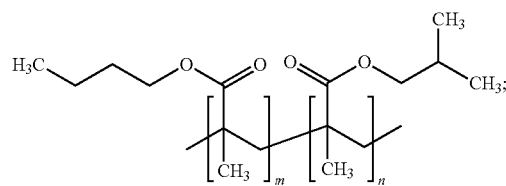

Poly(butyl methacrylate-co-methyl methacrylate):

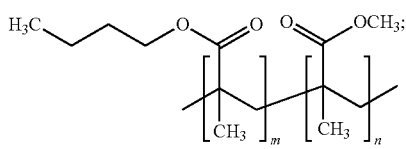

Poly(cyclohexyl methacrylate):

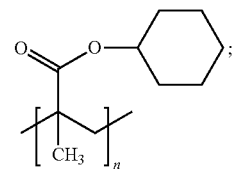

Poly[(2-ethyldimethylammonioethyl methacrylate ethyl sulfate)-co-(1-vinylpyrrolidone)]:

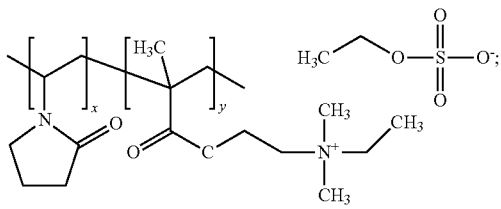

Poly(ethylene-co-glycidyl methacrylate):

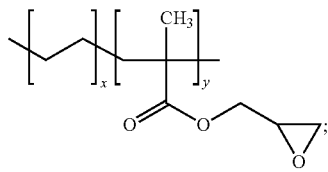

Poly(lauryl methacrylate-co-ethylene glycol dimethacrylate):

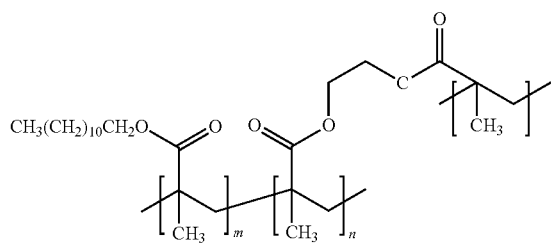

Poly(octadecyl methacrylate):

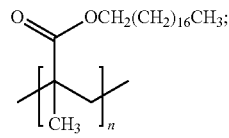

and
Poly(1-vinylpyrrolidone-co-2-dimethylaminoethyl methacrylate):

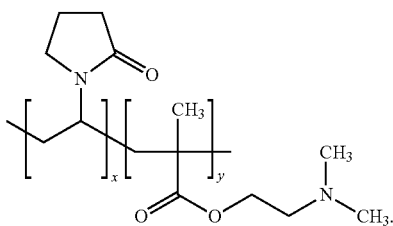

Curing

A person of ordinary skill in the art will also recognize that various methods may be used to cure resins in the present disclosure. Desirably, the curing occurs in situ in the presence of one or more metal containing materials in order to form polymeric materials with metallic nanoparticles.

In some embodiments, curing occurs by treating a resin with a chemical (i.e., chemical curing). In more specific embodiments, the resin is treated with one or more initiators, desirably in the presence of one or more metal containing materials. Non-limiting examples of suitable initiator systems include benzoyl peroxide (BPO) and dimethylparatoluidine (DMPT), and allyl thiourea (T) and cumene hydroperoxide (CH).

Initiators may be used at various concentrations and ratios for chemical curing. For instance, in some specific embodiments, chemical curing may consist of treating resins with allyl thiourea (T) and cumene hydroperoxide (CH). In other embodiments, chemical curing may consist of treating resins with benzoyl peroxide (BPO) and dimethylparatoluidine (DMPT).

In other embodiments, curing can occur by treating resins with a light source, such as ultraviolet or blue light (i.e., light curing). In other embodiments, curing may entail both light curing and chemical curing. Other methods of curing resins can also be envisioned by a person of ordinary skill in the art.

Applications

A person of ordinary skill in the art will recognize that the methods of the present disclosure can be used in various embodiments to form numerous anti-microbial resin compositions. For instance, in some embodiments, the methods of the present disclosure can be used to generate polymeric materials with silver nanoparticles (AgNP) by curing PMMA in the presence of silver benzoate (AgB).

FIG. 1 shows the change in color of a silver benzoate solution when combined with a solvent, dimethylaminoethyl methacrylate (DMAEMA) over time. As soon as the silver benzoate is added to DMAEMA, the solution appears clear at first (A) and then proceeds to become darker over time (B).

Figure 2:
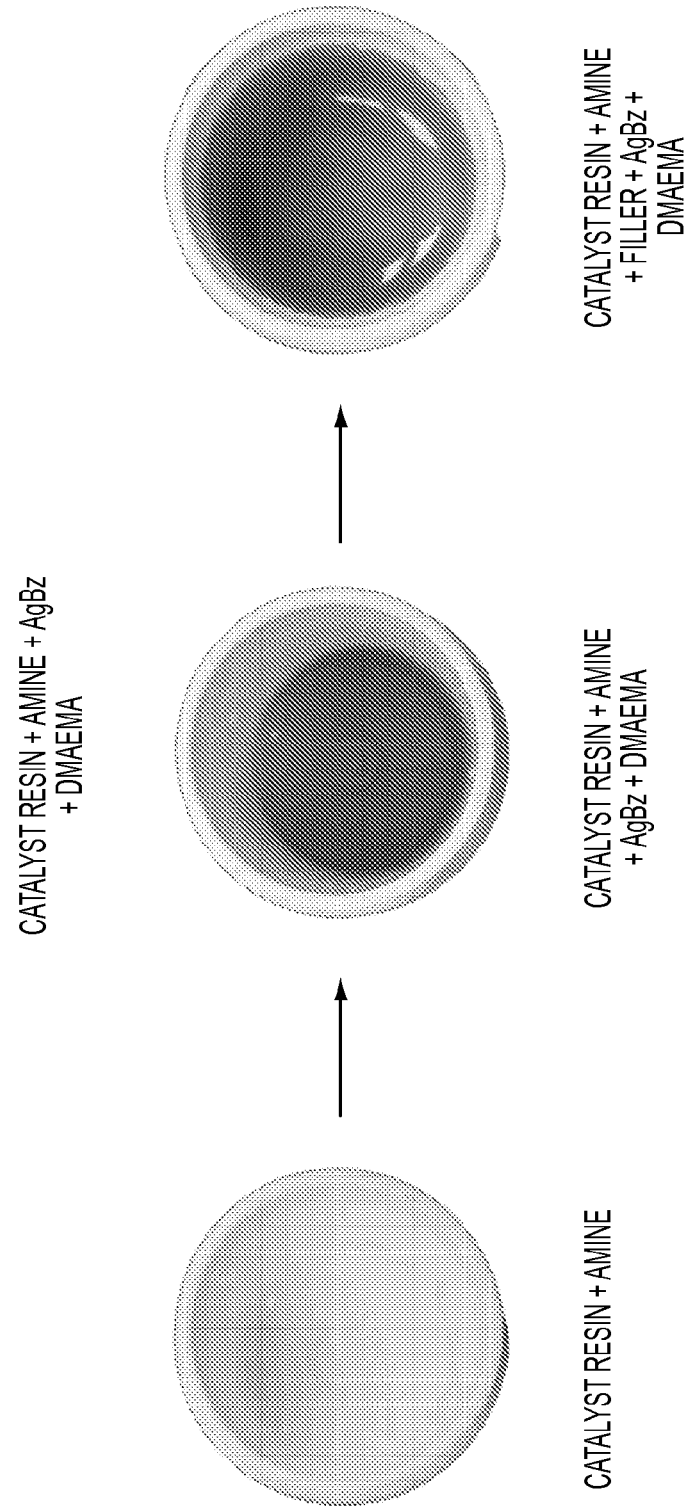
FIG. 2 shows the change in color of a catalyst resin.

FIG. 2 shows the change in color of a catalyst resin containing the self-cure amine upon addition of silver benzoate combined with DMAEMA. Initially, the catalyst resin with amine is clear in appearance, but becomes darker with the addition of silver benzoate in DMAEMA.

Figure 3:
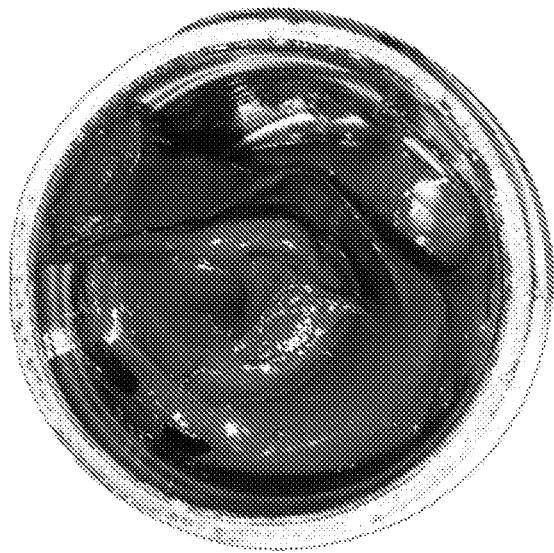
FIG. 3 shows the darkening and spontaneous self-polymerization of a catalyst resin.
Figure 4:
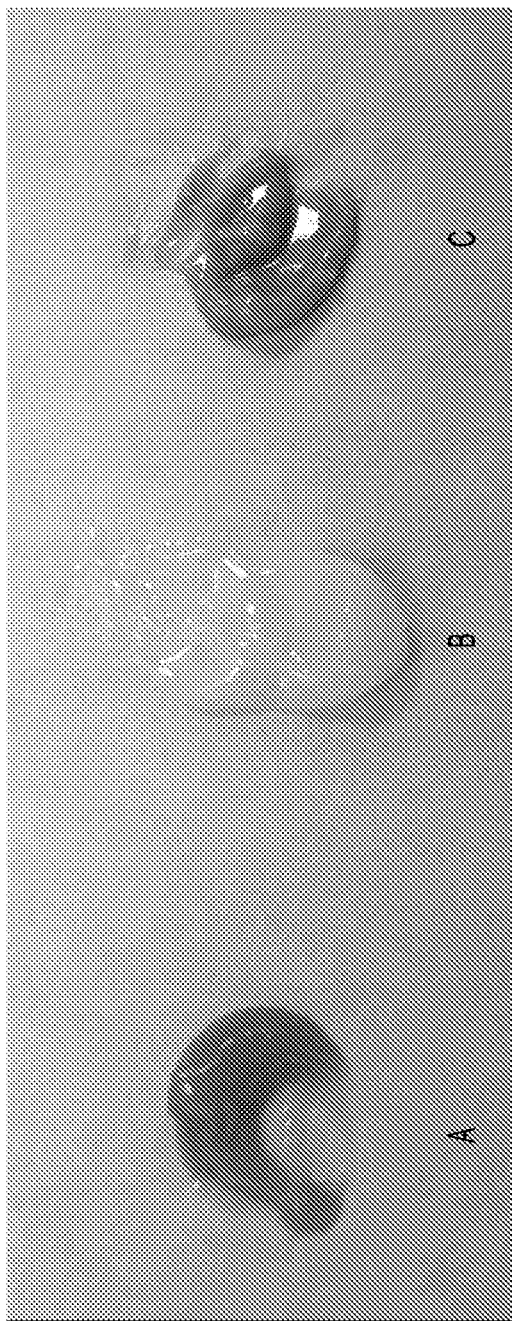
FIG. 4 shows the initial color of the base resin with benzoyl peroxide (A); the catalyst resin that contains photoinitiators (B), and catalyst resin with amine and silver benzoate (C)
Figure 5:
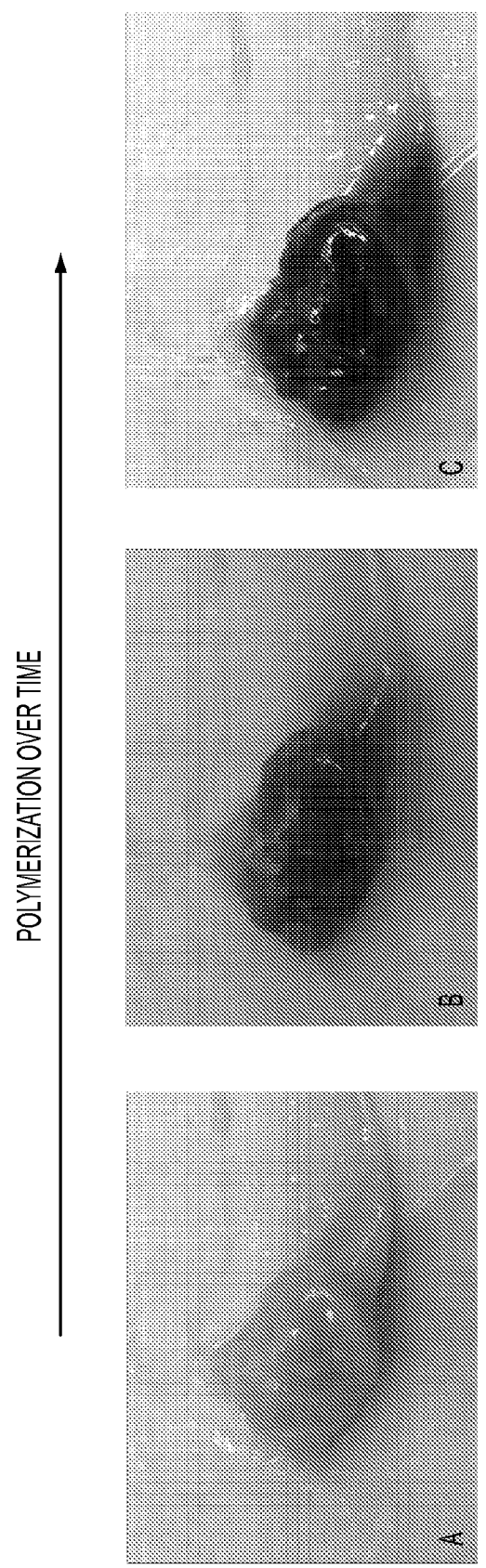
FIG. 5 shows the color shift of the resin over time after the mixture of silver benzoate containing DMAEMA and the catalyst resin is mixed with the base resin and polymerized at the time of mixing (A); after 30 seconds (B); and after less than one (1) minute (C)
Figure 6:
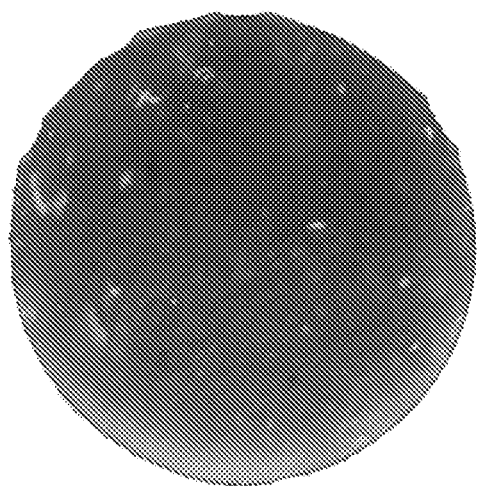
FIG. 6 a sample of the resin after polymerization is complete.

FIG. 3 shows the darkening and spontaneous self-polymerization of a catalyst resin containing silver benzoate combined with DMAEMA in accordance with methods of the invention. Over time, the catalyst resin with the addition of silver benzoate darkens and eventually polymerizes. FIG. 4 shows the initial color of the base resin with benzoyl peroxide (A), the catalyst resin that contains photoinitiators for the dual-cure resin (B), and when the silver benzoate containing DMAEMA is added to the catalyst resin (C);

FIG. 5 shows the color shift of the resin over time after the mixture of silver benzoate containing DMAEMA and the catalyst resin is mixed with the base resin and polymerized at the time of mixing (A); after 30 seconds (B); and after less than one (1) minute (C), while FIG. 6 shows a sample of the resin after polymerization is complete. FIGS. 5-6 demonstrate the color shift of the resin after the mixture of silver benzoate containing DMAEMA and the catalyst resin is mixed with the base resin and polymerized.

Figure 7:
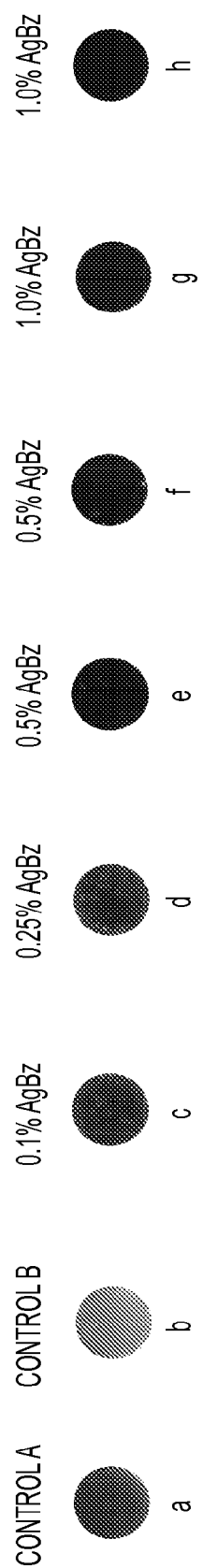
FIG. 7 shows the color profile of various resin compositions prepared by adding the silver benzoate/DMAEMA mixture to the catalyst resin portion.

FIG. 7 shows the color profile of various resin compositions prepared by adding the silver benzoate/DMAEMA mixture to the catalyst resin portion before mixing with the base resin portion to polymerize. The dark color of the final product is directly correlated with the amount of silver present.

Figure 8:
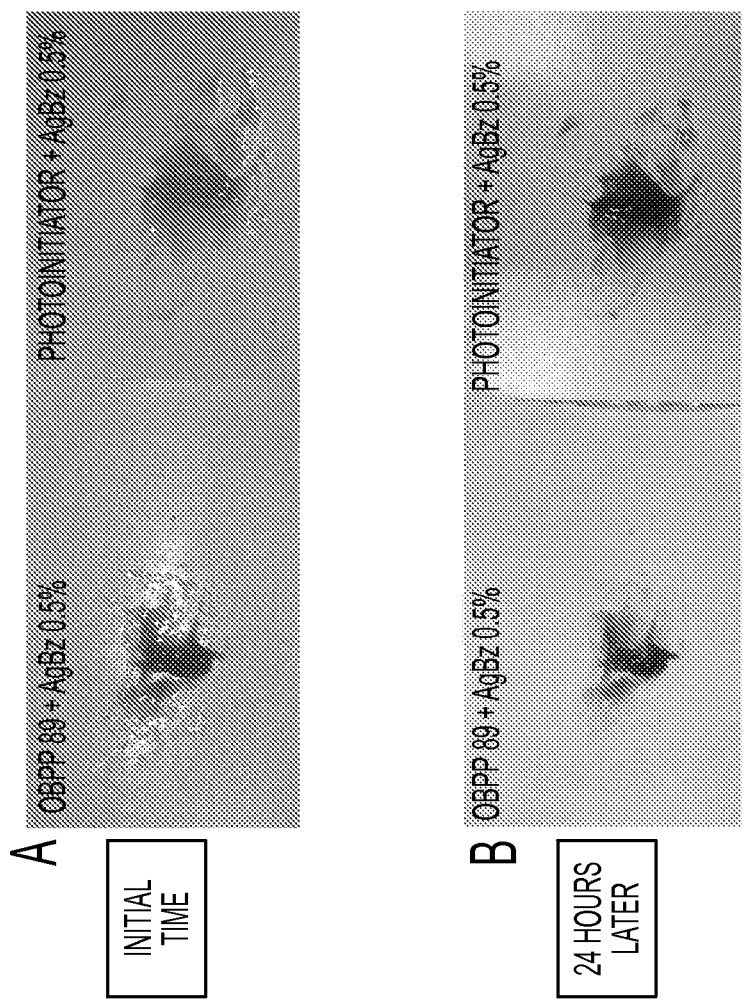
FIG. 8 shows the color profile of various resin compositions prepared by adding the silver benzoate/DMAEMA mixture to the base resin portion.

FIG. 8 shows the color profile of various resin compositions prepared by adding the silver benzoate/DMAEMA mixture to the base resin portion that when the silver benzoate/DMAEMA mixture is added to the base resin (instead of the catalyst resin), there is minimal color shift. When the photoinitiator is added, the color shifts more. After 24 hours, there is a slight color shift but it is significantly reduced compared to specimens where the silver benzoate/DMAEMA mixture is added to the catalyst resin.

Figure 9:
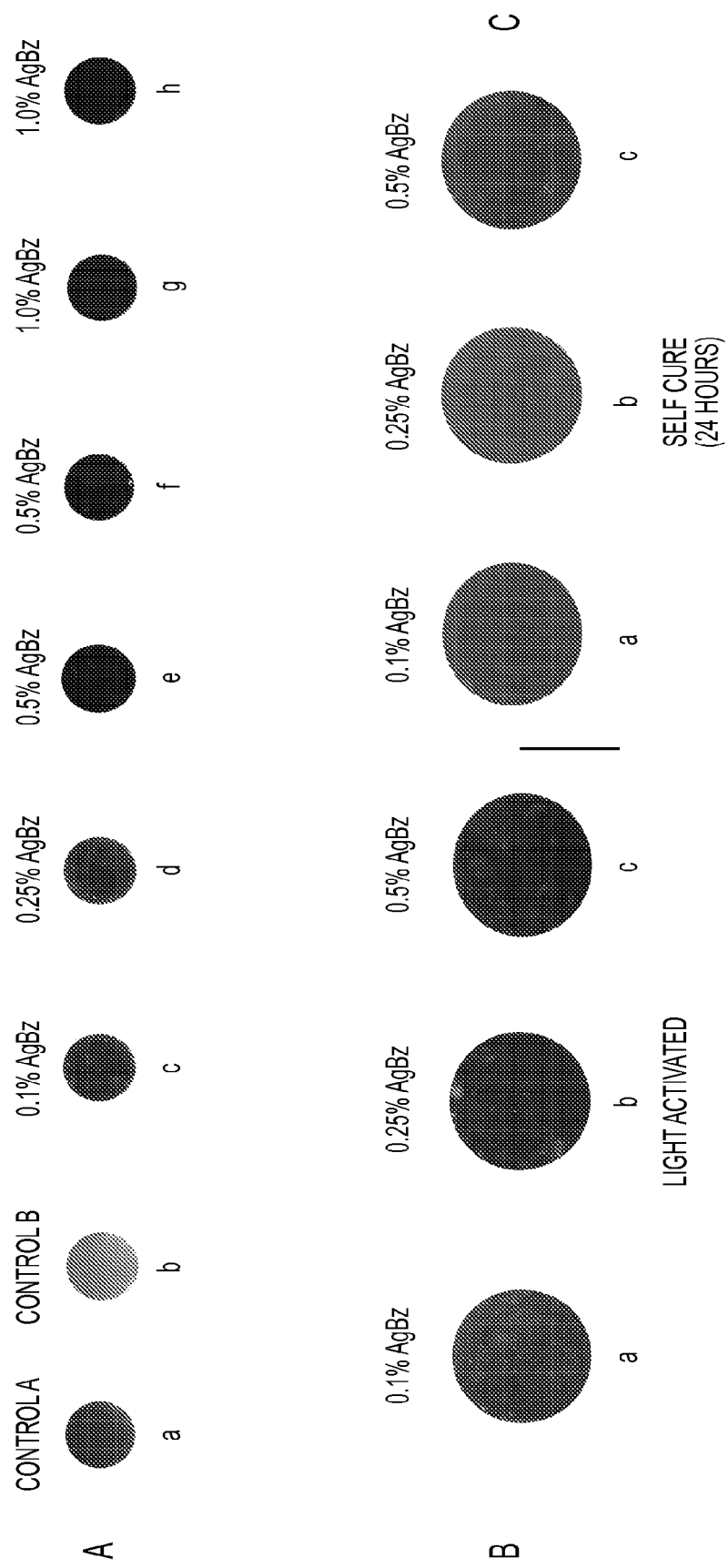
FIG. 9 compares the resin compositions of FIG. 7 (A) with the color profiles of various resin compositions prepared with the silver benzoate/DMAEMA mixture added to the base resin before mixing with the catalyst resin to polymerize and cured by either light-curing or self-curing (B)

FIG. 9 compares the resin compositions of FIG. 7 (A) with the color profiles of various resin compositions prepared with the silver benzoate/DMAEMA mixture added to the base resin before mixing with the catalyst resin to polymerize and cured by either light-curing or self-curing (B). The self-cured resins show how mixing the silver benzoate/DMAEMA mixture into the base resin instead of the catalyst resin greatly reduces the initial color of the resin samples. Additionally, after 24 hours, the color shift is not significant. The light-cured resins are significantly darker than the self-cured resins but still less-colored than resins prepared with the silver benzoate/DMAEMA mixture added to the catalyst resin. FIG. 10 demonstrates the effects of light on resin samples in the dark (A) and in the light (B). FIG. 11 demonstrates the effects of light on resin samples in the light (A) and in the dark (B). FIGS. 10-11 demonstrate that exposure to light will continue to darken the resin even if the silver benzoate/DMAEMA mixture is added to the base resin.

Figure 12:
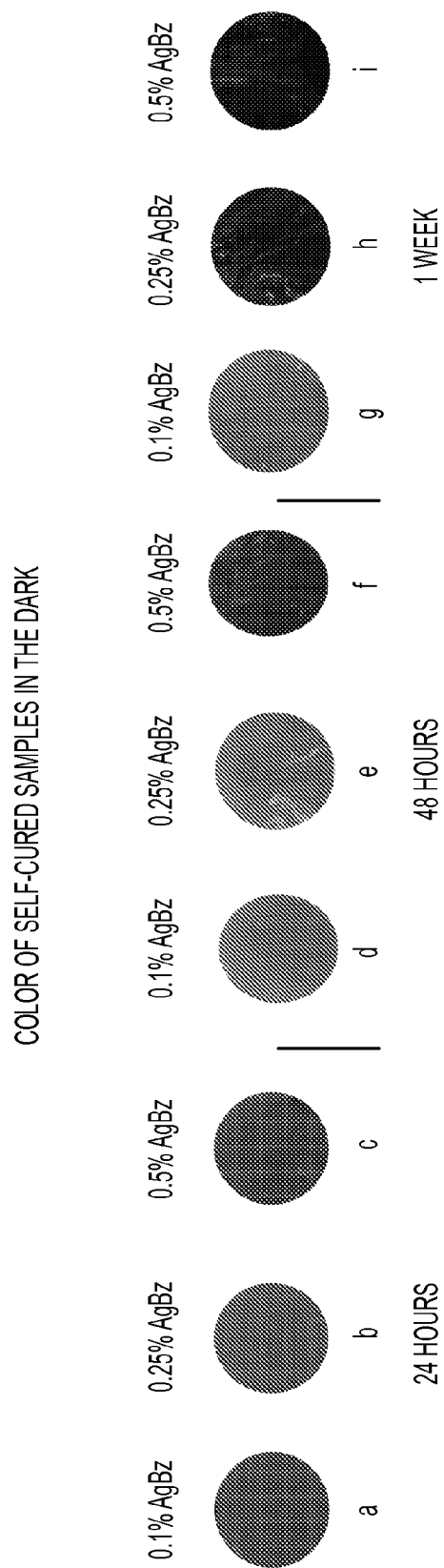
FIG. 12 demonstrates the reduced color shift of various resin compositions prepared in accordance with embodiments of the claimed invention, self-cured, and stored in the dark.

FIG. 12 demonstrates the reduced color shift of various resin compositions that are self-cured, and stored in the dark prepared in accordance with embodiments of the claimed invention.

Desirably, the methods of the present disclosure occur in situ. It is envisioned that curing resin compositions in situ can lead to more effective polymerization with improved nanoparticle dispersion, thereby producing more effective antimicrobial compositions.

An embodiment of the invention is directed to a method of making an antimicrobial resin composition containing silver nanoparticles, by selecting a silver-containing material, an acrylic resin monomer and a solvent that is miscible with the metal-containing material and with the acrylic resin monomer; combining the silver-containing material with the solvent to form a silver-containing material solution; mixing the silver-containing material solution with the acrylic resin monomer in situ to form an acrylic resin monomer solution; forming silver nanoparticles within the acrylic resin monomer solution by curing the acrylic resin monomer solution, wherein the curing process converts the acrylic resin monomer to a polymer; and forming an antimicrobial, resin composition.

In certain embodiments of the invention, the synthesized resin may be a dual cure resin or a self-cure resin that may be prepared using various combinations of resin monomers and suitable initiators. In various embodiments, herein disclosed are self-cure and dual-cure resins with silver nanoparticles that exhibit one or more of reduced color, reduced color shift, and/or reduced degree of self polymerization. In certain embodiments, compositions of the present invention comprise a camphorquinone (CQ) and 2-dimenthylaminoethyl methacrylate (DMAEMA). In other embodiments of the invention, other photo initiators and co-initiators such as iodomium initiators may also be used.

Embodiments of the claimed invention are directed to methods for making an antimicrobial resin composition containing silver particles and having a low initial color and reduced color shift over time. In order to achieve a final resin composition having low initial color and reduced color shift, the manner in which the polymerization is carried out is important. Typically, an antimicrobial resin composition comprising silver is prepared by combining a resin monomer with a solvent and an appropriate polymerization initiator along with a silver-containing material. However, depending upon the method, time and order of addition of the silver-containing material, the color profile of the final resin composition is affected.

In an embodiment of the invention, the silver-containing material is mixed with a solvent and added to the acrylic base resin component that does not contain an amine compound that exhibits a catalytic action, the latter being a common component used in chemical (self) cured polymerization systems. The base resin component used in this embodiment may be a self-cure or dual-cure resin.

In a further embodiment of the invention, the mixing of the silver-containing material with the base resin is carried out in the "dark" or under yellow light.

In a further embodiment of the invention, the silver-containing material and base resin mixture is mixed with catalyst resin, which comprises a catalytic amine compound. The mixing of the base resin containing the silver-containing material and the catalyst resin is preferably carried out in the dark or under yellow light.

In an embodiment of the invention, the final cured resin composition is stored in the dark or under yellow light in order to prevent darkening and extend the shelf life of the cured composition.

As is set forth in the figures, it is clear that the sequence of addition of the silver-containing material, i.e., adding it to the base resin component relative to the catalyst resin component is critical for determining several properties of the final resin composition including, but not limited to, initial color of the resin composition, color changes exhibited by the resin composition over time upon storage and premature spontaneous polymerization.

As shown in FIG. 1, a silver benzoate solution changes color over time when combined with a solvent, dimethylaminoethyl methacrylate (DMAEMA). FIGS. 4-6 demonstrate the color shift of the resin after silver benzoate containing DMAEMA is added to the catalyst resin followed by the addition of this mixture to the base resin for initiation of polymerization. In contrast, FIG. 9 shows the color profiles of various resin compositions prepared with the silver benzoate/DMAEMA mixture added to the base resin (instead of the catalyst resin) before mixing with the catalyst resin to polymerize and cured by either light-curing or self-curing. The self-cured resins show how mixing the silver benzoate/DMAEMA mixture into the base resin instead of the catalyst resin greatly reduces the initial color of the resin samples. Additionally, after 24 hours, the color shift is not significant.

In accordance with an embodiment of the invention, FIG. 8 shows that when the silver benzoate/DMAEMA mixture is added to the base resin, there is minimal color shift. When the photoinitiator is added, the color shifts more. After 24 hours, there is a slight color shift but it is significantly reduced compared to specimens where the silver benzoate/DMAEMA mixture is added to the catalyst resin prior to mixing with the base resin. FIG. 8 also shows that when the silver benzoate/DMAEMA mixture is added to the base resin, it does not spontaneously polymerize as it does when added to the catalyst resin (compare to FIG. 3).

In accordance with an embodiment of the invention, FIG. 12 demonstrates that when the resin compositions prepared in accordance with the methods described herein are both prepared and stored in the dark, they exhibit reduced color shift.

From the foregoing detailed description of specific embodiments of the invention, it should be apparent that novel antimicrobial polymeric materials and novel methods of making such materials have been disclosed. Although the invention has been described with reference to specific embodiments, these descriptions are not meant to be construed in a limiting sense. Various modifications of the disclosed embodiments, as well as alternative embodiments of the invention will become apparent to persons skilled in the art upon reference to the description of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. It is therefore contemplated that the claims will cover any such modifications or embodiments that fall within the true scope of the invention.

What is claimed is:

1. An antimicrobial resin composition comprising:
    a first resin that does not contain a catalytic amine;
    a silver-containing material dispersed in said first resin; and
    a second resin that is a self-curing catalytic resin.

2. The antimicrobial resin composition of claim 1, wherein said silver-containing material is selected from the group consisting of silver oleates, silver gluconates, silver adipates, silver sulfadiazines, silver benzoates and silver acetates.

3. The antimicrobial resin composition of claim 1, wherein said composition is used as a component of a medical device.

4. The antimicrobial resin composition of claim 3, wherein said medical device is a dental device.

* * * * *